US011241056B2

(12) United States Patent
Bell et al.

(10) Patent No.: US 11,241,056 B2
(45) Date of Patent: Feb. 8, 2022

(54) REPLACEABLE EARMUFFS

(71) Applicant: The Bell System LLC, Livingston, MT (US)

(72) Inventors: Alison Bell, Livingston, MT (US); Frederick Bell, Livingston, MT (US)

(*) Notice: Subject to any disclaimer, the term of this patent is extended or adjusted under 35 U.S.C. 154(b) by 155 days.

(21) Appl. No.: 15/931,449

(22) Filed: May 13, 2020

(65) Prior Publication Data
US 2021/0352988 A1 Nov. 18, 2021

(51) Int. Cl.
*A42B 1/0188* (2021.01)

(52) U.S. Cl.
CPC ................................. *A42B 1/0188* (2021.01)

(58) Field of Classification Search
CPC ..... A42B 1/0188; A42B 1/0186; A42B 1/245; A42B 3/16; A42B 3/163; A42B 3/166; A42B 3/30; A42B 3/306; A61F 11/14; H04R 1/10; H04R 1/1008; H04R 1/105; H04R 1/1058; H04R 1/1066; H04R 1/1091; H04R 1/12; A45D 44/12; A63B 71/10
USPC ...................... 2/209, 423; 128/866, 867, 864
See application file for complete search history.

(56) References Cited

U.S. PATENT DOCUMENTS

| 2,149,383 A | 5/1937 | Bean | |
| 2,314,782 A * | 3/1943 | Goretsky | A61F 11/06 |
| | | | 2/209 |
| 2,447,078 A * | 8/1948 | Maxant | A61F 11/06 |
| | | | 2/209 |
| 3,456,263 A * | 7/1969 | Aileo | A61F 11/14 |
| | | | 2/423 |
| 3,477,067 A * | 11/1969 | Aileo | A42B 3/166 |
| | | | 2/209 |
| 3,833,939 A * | 9/1974 | Dostourian | H04R 1/1066 |
| | | | 2/209 |
| 4,546,215 A | 10/1985 | Ferraro | |
| 4,654,898 A | 4/1987 | Ishikawa | |
| 5,148,887 A * | 9/1992 | Murphy | A42B 3/166 |
| | | | 181/129 |
| 5,509,146 A | 6/1996 | Bryerton, Sr. | |
| 5,898,945 A | 5/1999 | Weiser | |
| 6,016,574 A * | 1/2000 | Chen | A42B 1/0188 |
| | | | 2/209 |

(Continued)

FOREIGN PATENT DOCUMENTS

| CN | 201805531 U | * | 4/2011 |
| CN | 208971763 U | * | 6/2019 |
| CN | 212876089 U | * | 4/2021 |

*Primary Examiner* — Amy Vanatta
(74) *Attorney, Agent, or Firm* — Antoinette M. Tease

(57) ABSTRACT

A replaceable earmuff system with an arch-shaped member (headband) and first and second earmuff assemblies that are removably attached to the arch-shaped member. Each earmuff assembly has inner and outer earmuff housings and a spring. The inner earmuff housing is circular in shape with a flat base plate and a lip that extends around the perimeter of a first side of the inner earmuff housing. A circular protrusion, which has two opposing L-shaped slots, is situated in the center of the inner earmuff housing on a second side of the inner earmuff housing. The outer earmuff housing is saucer-shaped with a concave inner side and a convex outer side. A circular collar with two opposing keys that fit within the L-shaped slots is situated in the center of the concave inner side of the outer earmuff housing. The spring fits within the circular protrusion and the circular collar.

10 Claims, 7 Drawing Sheets

(56) References Cited

U.S. PATENT DOCUMENTS

| | | | |
|---|---|---|---|
| 6,392,196 B1 * | 5/2002 | Lin | A61F 11/14 2/209 |
| 6,625,819 B1 * | 9/2003 | Tsai | A61F 11/14 181/129 |
| 6,888,950 B2 * | 5/2005 | Siskin | A61F 11/14 381/378 |
| 79,969,263 | 8/2011 | Isom et al. | |
| 8,438,666 B2 | 5/2013 | Le Gette | |
| 9,113,259 B2 * | 8/2015 | Pan | H04S 3/004 |
| 2019/0116411 A1 * | 4/2019 | Duckwall | H04R 1/1016 |

* cited by examiner

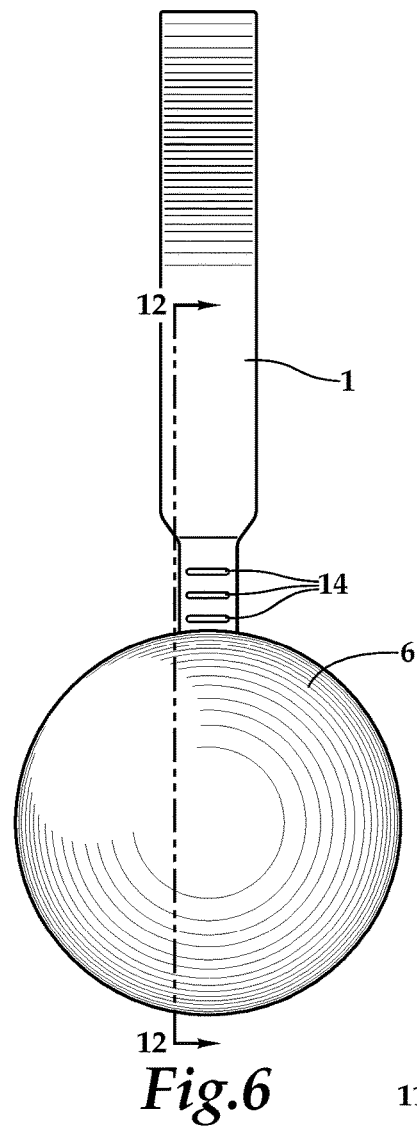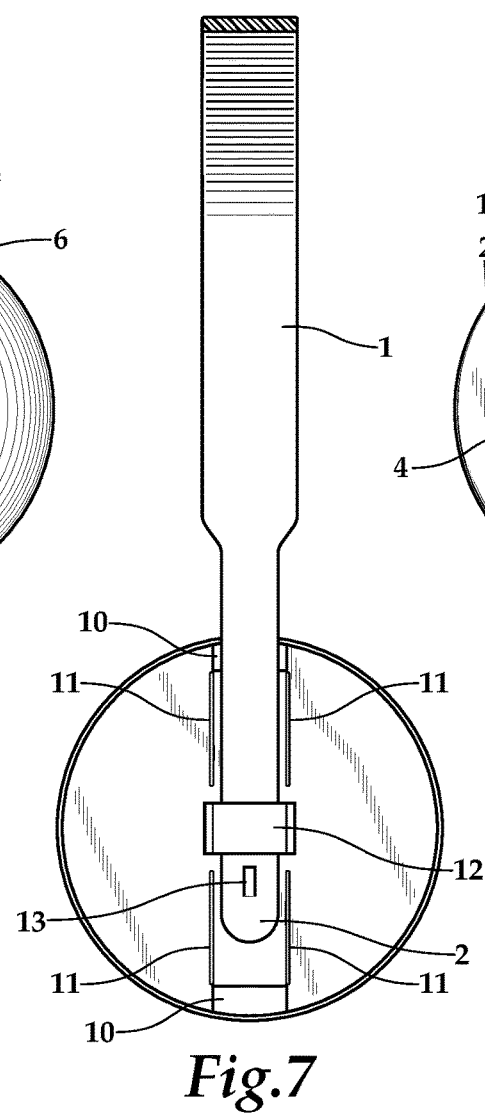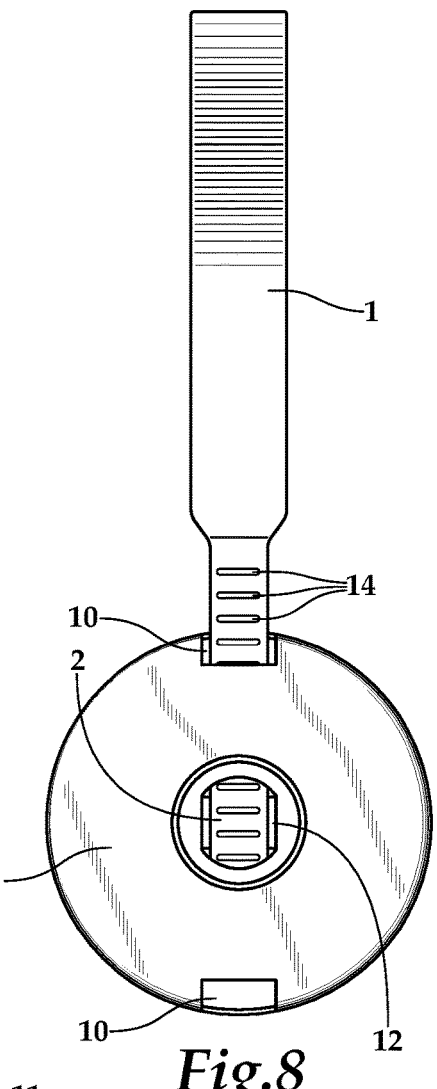

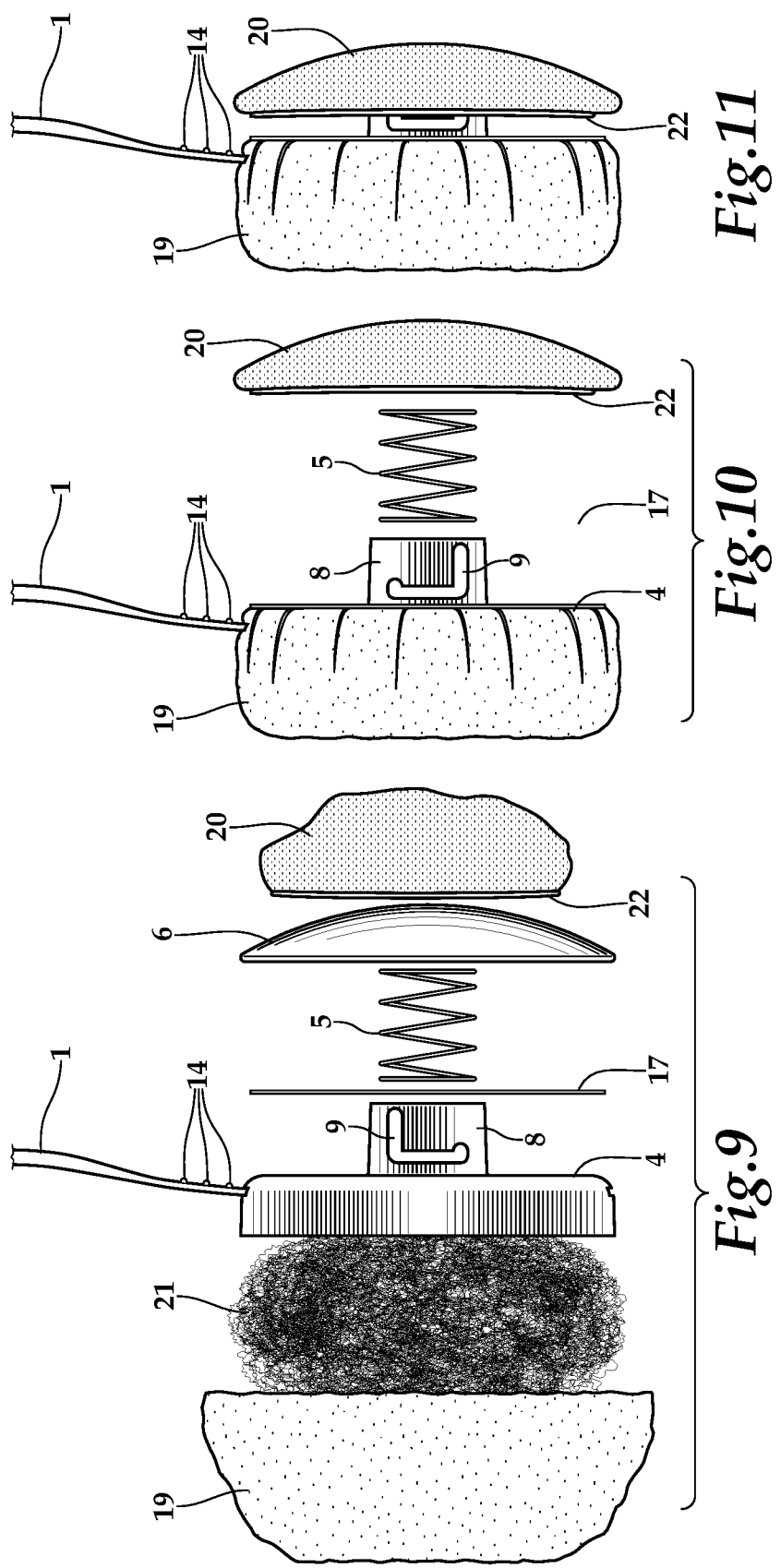

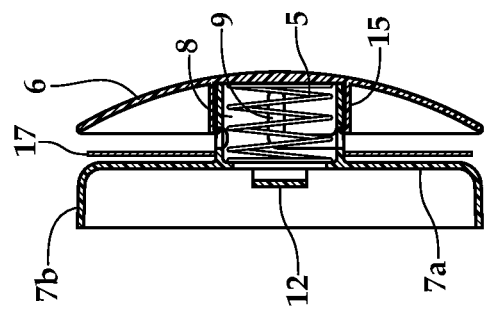
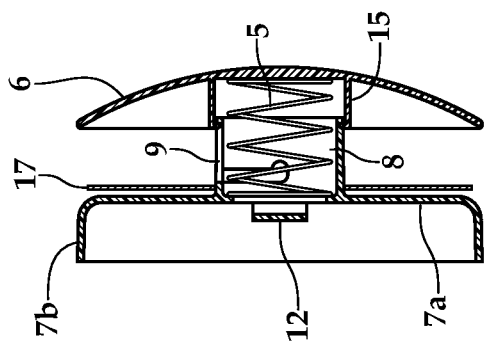
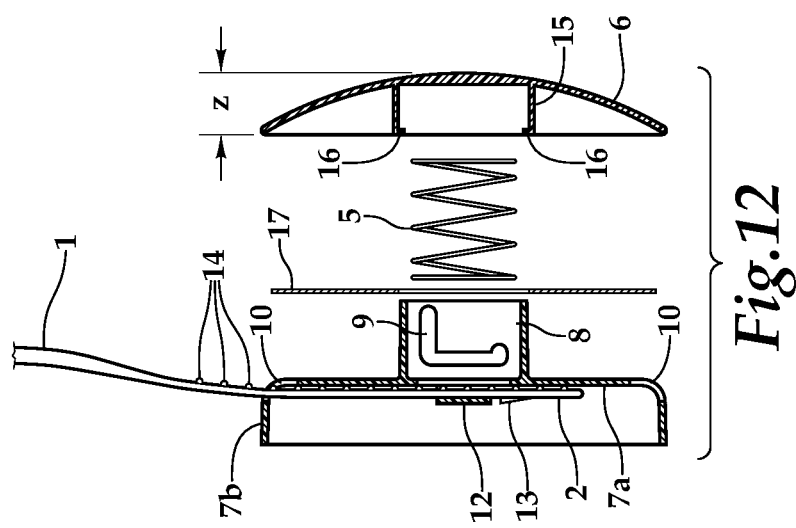

REPLACEABLE EARMUFFS

BACKGROUND OF THE INVENTION

1. Field of the Invention

The present invention relates generally to the field of headwear, and more particularly, to earmuffs in which the earmuff coverings are replaceable.

2. Description of the Related Art

The present invention provides a unique solution to the problem of having to purchase and own multiple different sets of earmuffs for different outfits, events, seasons or moods. With the present invention, the fabric covering on the earmuffs is easily replaceable, which means that a person need only own a single pair of earmuffs with a multitude of different fabric covers. The present invention is designed without any pivot points that might become loose or any detachable parts that may become lost or misplaced. With the present invention, the outer fabric covering is removed with a quick and simple twisting motion of the hand. Although others have tried to solve the same problem, there is nothing in the prior art that is structurally similar to the present invention.

U.S. Pat. No. 2,149,383 (Bean, 1937) discloses an earmuff with oval supports. The oval supports are a pair of ring-like wire frames that are pivotally attached to an arch-shaped member. A fabric covering that is smooth on one side and preferably comprised of fur on the other side is reversibly placed over the wire frames.

U.S. Pat. No. 4,546,215 (Ferraro, 1985) provides detachable earmuffs for headsets in which a pair of frames is removably attached to the headband. Each frame comprises a pair of arms that may be resiliently flexed to remove the frame from the headband. The arms are biased so that the entrance separation in the frame is ordinarily closed.

U.S. Pat. No. 4,654,898 (Ishikawa, 1987) discloses removable earmuffs for headphones. Each earmuff is constructed with a support cup that is covered by fabric. The band for the headphone speaker is secured by two overlapping flaps that extend over the band and are locked together by mating plastic hook-and-loop fasteners.

U.S. Pat. No. 5,509,146 (Bryerton, Sr., 1996) provides earmuffs with an adjustable headband and ear pieces with removable discs on the outwardly facing sides of the ear pieces. Ear cushions with a noise muffling material are removably attached to the inwardly facing sides of the ear pieces.

U.S. Pat. No. 589,894 (Weiser, 1999) discloses an earmuff that is snappably engaged with the ear of the wearer. The earmuff has an outer cover and an inner snappable annular actuating element that is form-fitted within the outer cover. The inner annular actuating element has a C-shaped closable ribbon-like member that effectively changes the shape of the actuating element from a "C" to an "0." The earmuffs optionally include small audio transducers, which act as earphones.

U.S. Pat. No. 7,996,923 (Isom el al., 2011) provides an ear warmer device with an ear warmer frame. A set of membranes are coupled together, or a single member is folded over, to form a shell into which the frame is inserted. The frame is comprised of first, second and third frame members, the second frame member having a plurality of projections that facilitates the coupling of the three frame members.

U.S. Pat. No. 8,438,666 (Le Gette, 2013) discloses an adjustable ear warmer comprised of first and second bands attached to a frame. The first and second bands are slidably movable relative to each other so that the overall length of the headband can be adjusted.

BRIEF SUMMARY OF THE INVENTION

The present invention is a replaceable earmuff system comprising: an arch-shaped member configured to fit over a wearer's head, the arch-shaped member comprising a first terminal end and a second terminal end; a first earmuff assembly that is removably attached to the first terminal end of the arch-shaped member; a second earmuff assembly that is removably attached to the second terminal end of the arch-shaped member; and a spring; wherein each of the first and second earmuff assemblies comprises an inner earmuff housing, a spring, and an outer earmuff housing; wherein the inner earmuff housing is circular in shape and comprises a flat base plate and a lip that extends around a perimeter of a first side of the inner earmuff housing, the lip being perpendicular to the flat base plate; wherein a circular protrusion is situated in a center of the inner earmuff housing on a second side of the inner earmuff housing; wherein the circular protrusion comprises two opposing L-shaped slots; wherein the flat base plate comprises two opposing slots situated between the flat base plate and the lip; wherein the outer earmuff housing is saucer-shaped with a concave inner side and a convex outer side; wherein a circular collar is situated in a center of the concave inner side of the outer earmuff housing; wherein the circular collar has an inner diameter; wherein the circular protrusion on the inner earmuff housing has an outer diameter; wherein the inner diameter of the circular collar is greater than the outer diameter of the circular protrusion; wherein the circular collar comprises two opposing keys that are configured to fit within the L-shaped slots in the circular protrusion; and wherein the spring is configured to fit within the circular protrusion on the inner earmuff assembly and within the circular collar on the outer earmuff assembly when the system is fully assembled.

In a preferred embodiment, the circular protrusion has a diameter, the flat base plate has a diameter, and the diameter of the circular protrusion is less than half of the diameter of the flat base plate. Preferably, the flat base plate has an outer surface, and the walls of the circular protrusion are perpendicular to the outer surface of the flat base plate.

In a preferred embodiment, the first side of the inner earmuff housing comprises two pairs of guide members that are configured to form a channel; wherein each pair of guide members comprises two guide members oriented parallel to one another; wherein the two pairs of guide members are oriented so that one pair of guide members is linearly aligned with the other pair of guide members; wherein the first and second terminal ends of the arch-shaped member each has a width; wherein the width of the first terminal end is equal to the width of the second terminal end; wherein there is a distance between each guide member in each pair of guide members; and wherein the distance between each guide member in each pair of guide member is equal to or greater than the width of the first or second terminal end of the arch-shaped member. Preferably, a bracket is situated between the two pairs of guide members and configured to receive the first or second terminal end of the arch-shaped member; wherein the first pair of guide members, the bracket, the second pair of guide members, and the opposing slots that are situated between the flat base plate and the lip of the flat base plate are all linearly aligned along a central axis of the inner earmuff housing.

In a preferred embodiment, the inner earmuff housing has an outer diameter; wherein the outer earmuff housing has an outer diameter; and wherein the outer diameter of the inner earmuff housing equals the outer diameter of the outer earmuff housing. Preferably, the circular collar has a height; wherein the circular protrusion has a height; and wherein the height of the circular collar is less than the height of the circular protrusion.

In one embodiment, the invention further comprises a cover plate; wherein the cover plate has an outer diameter that is equal to the outer diameter of the inner earmuff housing and the outer diameter of the outer earmuff housing; wherein the cover plate comprises a central bore with an inner diameter that is greater than the outer diameter of the circular protrusion; and wherein the cover plate is affixed to an outside surface of the inner earmuff housing between the inner earmuff housing and the outer earmuff housing. In another embodiment, the invention further comprises an inner fabric covering that is configured to fit over the inner earmuff assembly and an outer fabric covering that is configured to fit over the outer earmuff assembly.

In a preferred embodiment, each of the L-shaped slots in the circular protrusion comprises: a first leg that extends perpendicularly to the flat base plate; a second leg with a first end and a second end, the first end of the second leg being connected to the first leg, and the second leg extending parallel to the flat base plate; and a tub that extends from the second end of the second leg in parallel with the first leg.

BRIEF DESCRIPTION OF THE DRAWINGS

FIG. 6 is a first side view of the present invention taken from the perspective shown in FIG. 5. The inner and outer fabric coverings have been omitted from this figure for clarity.

FIG. 7 is a section view of the present invention taken from the perspective shown in FIG. 5. The inner and outer fabric coverings have been omitted from this figure for clarity.

FIG. 8 is a second side view of the present invention taken from the perspective shown in FIG. 5. The inner and outer fabric coverings have been omitted from this figure for clarity.

FIG. 9 is an exploded side view of one of the earmuff assemblies of the present invention.

FIG. 10 is a partially exploded side view of one of the earmuff assemblies of the present invention shown with the inner fabric covering and batting installed on the inner earmuff housing.

FIG. 11 is a side view of one of the earmuff assemblies of the present invention shown in a fully assembled and closed position.

FIG. 12 is an exploded section view of one of the earmuff assemblies. The inner and outer fabric coverings have been omitted from this figure for clarity.

FIG. 13 is a section view of one of the earmuff assemblies shown with the earmuff assembly in an open position. The inner and outer fabric coverings have been omitted from this figure for clarity.

FIG. 14 is a section view of one of the earmuff assemblies shown with the earmuff assembly in a closed position. The inner and outer fabric coverings have been omitted from this figure for clarity.

REFERENCE NUMBERS

Figure 1:
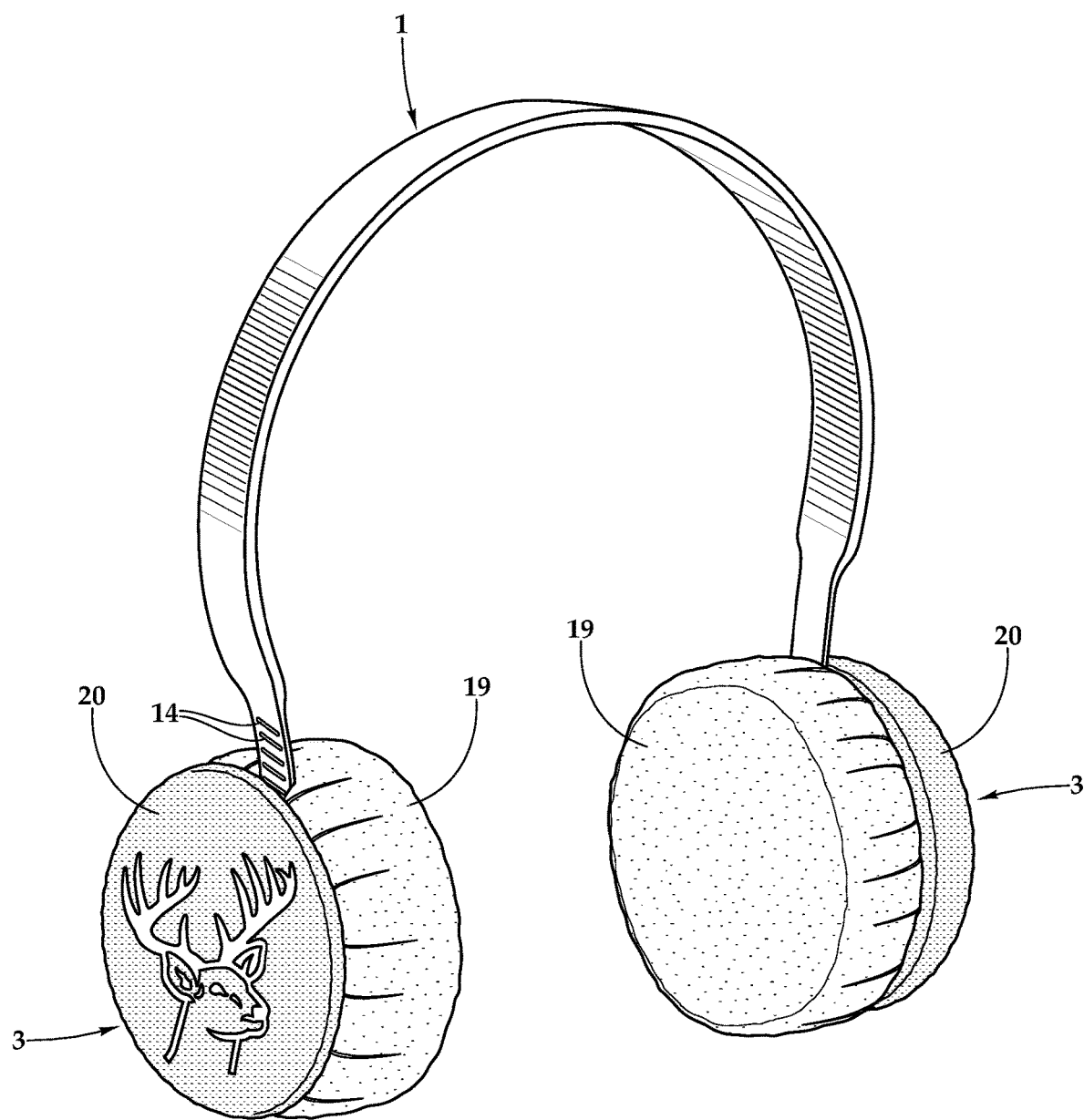
FIG. 1 is perspective view of the present invention.

1 Arch-shaped member (headband)
2 Terminal end (of arch-shaped Member)
3 Earmuff assembly
4 Inner earmuff housing
5 Spring
6 Outer earmuff housing
7a Flat base plate (of inner earmuff housing)
7b Lip (of inner earmuff housing)
8 Circular protrusion
9 L-shaped slots (in circular protrusion)
9a First leg (of L-shaped slot)
9b Second leg (of L-shaped slot)
9c Tab (of L-shaped slot)
10 Opposing slots (in inner earmuff housing)
11 Guide members (on inner earmuff housing)
12 Bracket (on inner earmuff housing)
13 Stop (on terminal end of arch-shaped member)
14 Ridges (on terminal end of arch-shaped member)
15 Circular collar (on outer earmuff housing)
16 Key (on circular collar)
17 Cover plate
18 Central bore (of cover plate)
19 Inner fabric covering
20 Outer fabric covering
21 Filler material
22 Elasticized outer perimeter (of outer fabric covering)

DETAILED DESCRIPTION OF INVENTION

FIG. 1 is perspective view of the present invention. As shown in this figure, the present invention is comprised of an arch-shaped member 1 (or headband) configured to fit over the head of a wearer. The arch-shaped member 1 comprises first and second terminal ends 2 disposed on each end of the arch-shaped member 1. As described more fully below, the first and second terminal ends 2 of the arch-shaped member are removably attached to first and second earmuff assemblies 3.

Figure 2:
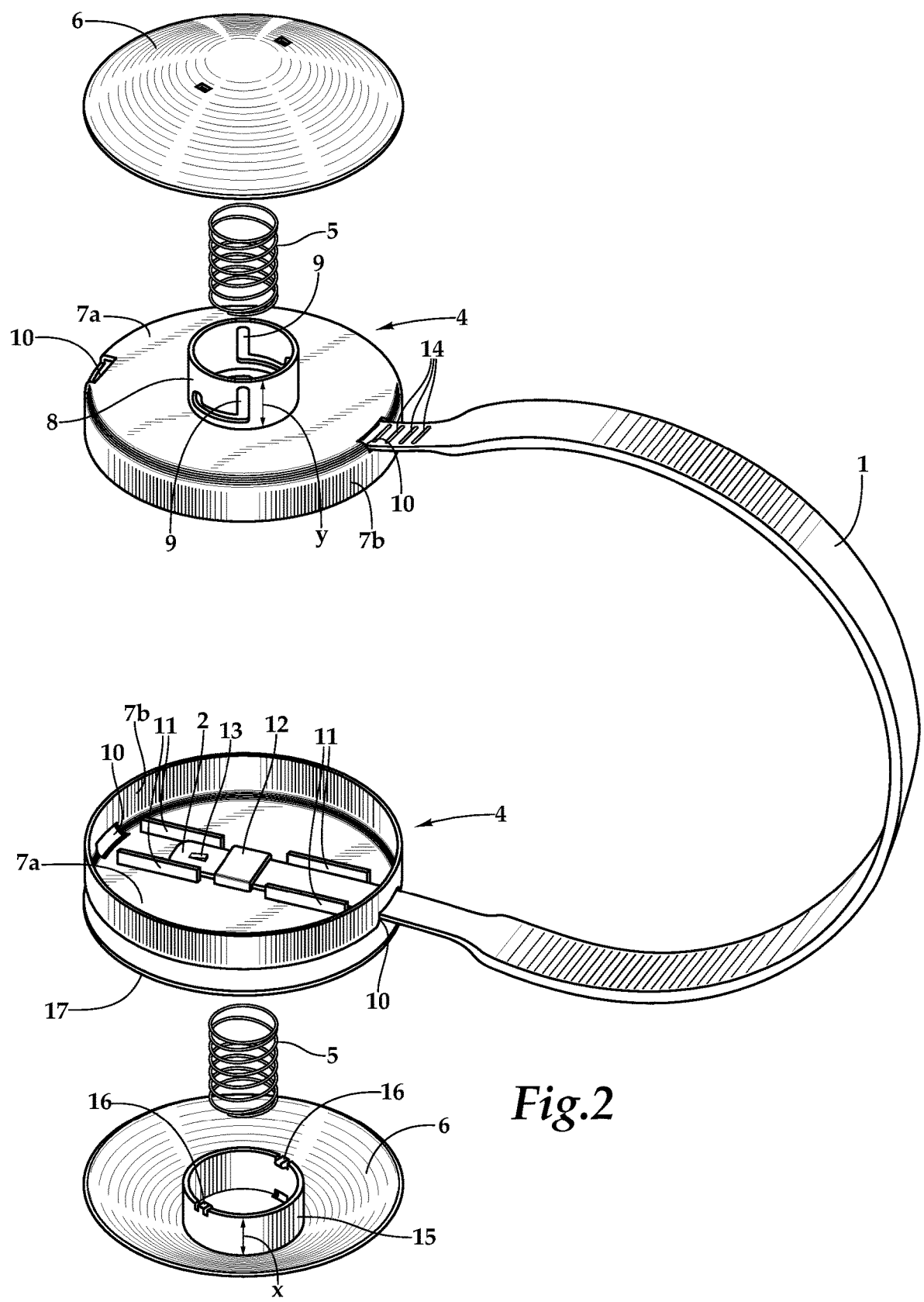
FIG. 2 is an exploded perspective view of the present invention. The inner and outer fabric coverings have been omitted from this figure for clarity.

FIG. 2 is an exploded perspective view of the present invention. As noted above, the inner and outer fabric coverings have been omitted from this figure for clarity. Each earmuff assembly 3 comprises an inner earmuff housing 4, a spring 5, and an outer earmuff housing 6. As shown in this figure, the inner earmuff housing 4 is circular in shape and comprises a flat base plate 7a and a lip 7b that extends around the perimeter of a first side of the inner earmuff housing, the lip 7b being perpendicular to the flat base plate 7a. A circular protrusion 8 is situated in the center of the inner earmuff housing 4 on a second side of the inner earmuff housing. The diameter of the circular protrusion 8 is less than half of the diameter of the flat base plate 7a. The walls of the circular protrusion 8 are perpendicular to the outer surface of the flat base plate 7a.

The circular protrusion comprises opposing L-shaped slots 9 whose function will be described more fully below. At the point at which the flat base plate 7a joins the lip 7b, the inner earmuff housing 4 comprises opposing slots 10, the purpose of which is to receive the first or second terminal end 2 of the arch-shaped member 1. The first side of the inner earmuff housing (that is, the same side of the inner earmuff housing from which the lip 7b extends) comprises two pairs of guide members 11 that are configured to form a channel through which the first or second terminal end 2 of the arch-shaped member 1 is inserted, as shown. Each pair of guide members 11 comprises two guide members oriented parallel to one another, and the two pairs of guide members are oriented so that one pair of guide members is linearly aligned with the other pair of guide members to effectively form a channel through which the terminal end 2 extends. The distance between each guide member in each pair of guide members 11 is preferably approximately equal to or only slightly greater than the width of the terminal end 2 of the arch-shaped member 1.

The two pairs of guide members are spaced apart from one another to accommodate a bracket 12 that is configured to secure the terminal end 2 of the arch-shaped member 1. This bracket 12 is situated between the two pairs of guide members 11, and the first pair of guide members 11, the bracket 12, and the second pair of guide members 11 are all linearly aligned along a central axis of the inner earmuff housing 4. The opposing slots 10 in the inner earmuff housing 4 are also aligned along this same central axis so that the terminal end 2 of the arch-shaped member 1 may be inserted into either of the slots 10, through either the first or second pair of guide members 11, and into the bracket 12, thereby securing the inner earmuff housing on the terminal end of the arch-shaped member.

A stop 13 on the terminal end 2 of the arch-shaped 1 abuts up against the bracket 12 when the terminal end is in the position shown in FIG. 2, thereby preventing the terminal end 2 from coming out of the bracket 12. A plurality of ridges 14 situated on an outer surface of the arch-shaped member 1 proximate to the terminal end 2 allow the fit of the arch-shaped member 1 on the head of a wearer to be adjusted by pushing the terminal end 2 further down into the guide members 11. The ridges 14 prevent the terminal end 2 from simply sliding up and down within the guide members, and some level of manual force is required to overcome the friction between the ridges 14 and the inner earmuff housing 4.

The outer earmuff housing 6 is saucer-shaped such that the outer earmuff housing 6 has a concave (inner) side and a convex (outer) side. The outer diameter of the outer earmuff housing 6 is preferably the same as the outer diameter of the inner earmuff housing 4. Situated in the center of the concave (inner) side of the outer earmuff housing 6 is a circular collar 15 with an inner diameter that is only slightly greater than the outer diameter of the circular protrusion 8 on the inner earmuff housing 4. The height of the circular collar 15 (designated as "x" on FIG. 2) is preferably less than the height of the circular protrusion 8 (designated as "y" on FIG. 2). The circular collar 15 two opposing keys 16, which are designed to fit within the L-shaped slots 9 in the circular protrusion 8, as explained more fully below. When fully assembled, the circular protrusion 8 acts as a female piece that fits within the circular collar 15 to form a fastening mechanism between the inner earmuff housing 4 and the outer earmuff housing 6. Note that the optional cover plate 17 (discussed in connection with Figure X below) has been omitted from the top earmuff assembly 2 in FIG. 2 for clarity, but it is shown in the bottom earmuff assembly in that figure.

Figures 3, 4:
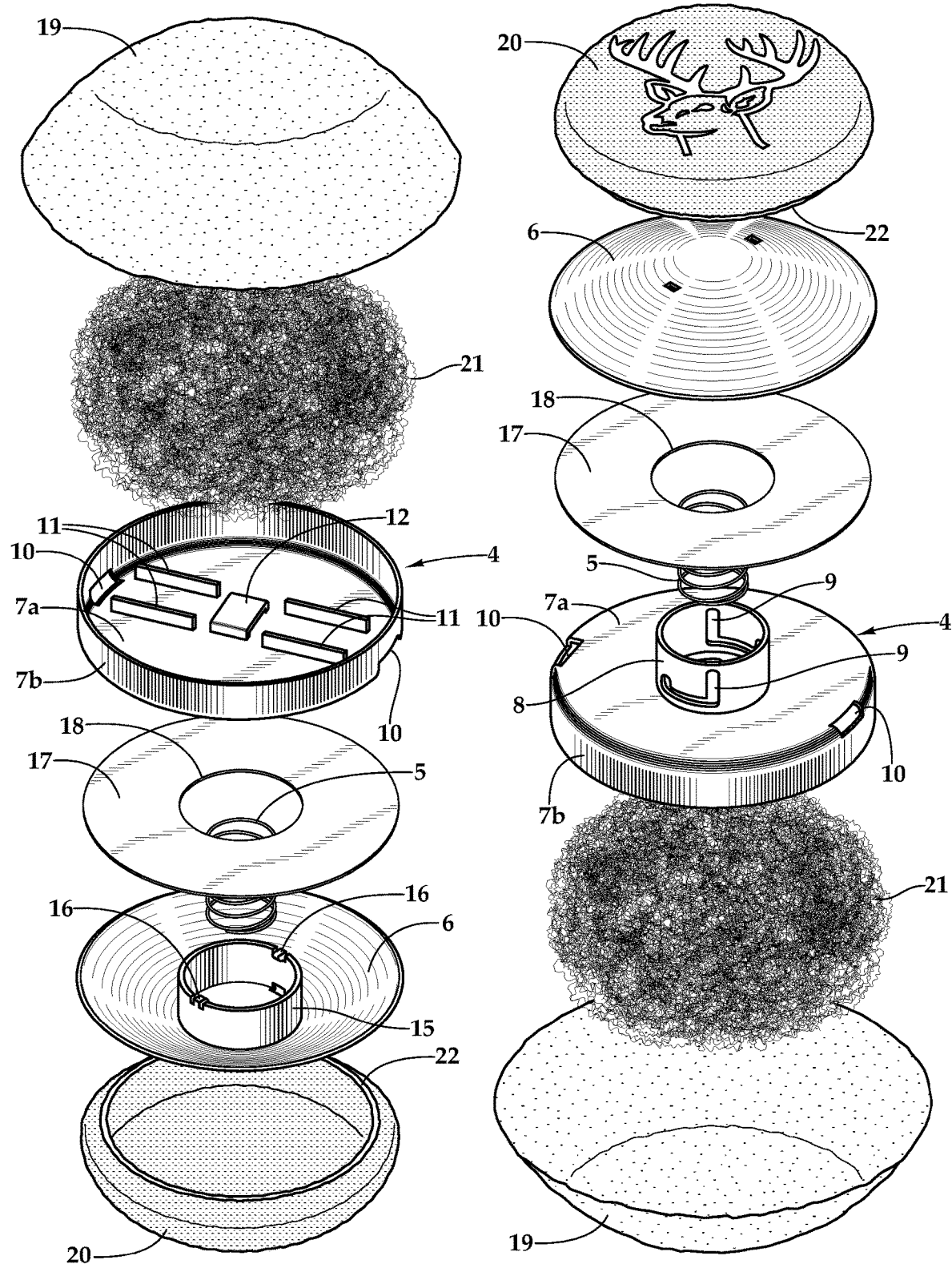
FIG. 3 is a first exploded perspective view of one of the earmuff assemblies of the present invention.
FIG. 4 is a second exploded perspective view of one of the earmuff assemblies of the present invention.

FIG. 3 is a first exploded perspective view of one of the earmuff assemblies of the present invention. This figure shows an optional cover plate 17 juxtaposed between the inner earmuff housing 4 and the outer earmuff housing 6. The optional cover plate 17 has the same outer diameter as the inner earmuff housing 4 and the outer earmuff housing 6 and comprises a central bore 18 with an inner diameter that is slightly greater than the outer diameter of the circular protrusion 8. The purpose of the cover plate 17 is to cover that part of the inner earmuff housing 4 to which the inner fabric covering 19 is adhered.

FIG. 4 is a second exploded perspective view of one of the earmuff assemblies of the present invention. This figure provides a different perspective view of the same components described above in connection with FIG. 3. Note that the outer perimeter of the flat base plate 7a of the inner earmuff housing 4 is preferably rounded or beveled, as shown.

As shown in FIGS. 3 and 4, the present invention preferably comprises inner and outer fabric coverings. The inner fabric covering 19 is configured to fit around the inner earmuff housing 4 and is preferably affixed to the inner earmuff housing with glue or another form of adhesive. A filler material 21, which may take the form of batting, a foam insert, or any other suitable material, is placed in between the inner fabric covering 19 and the inner earmuff housing 4 (within the lip 7b) to provide comfort to the wearer. The outer fabric covering 20 preferably comprises an elasticized outer perimeter 22 so that the outer fabric covering 20 may be easily slipped over the convex (outer) surface of the outer earmuff housing 6. The present invention is designed to allow one outer fabric covering 20 to be removed and replaced with another outer fabric covering without disassembling the unit.

Figure 5:
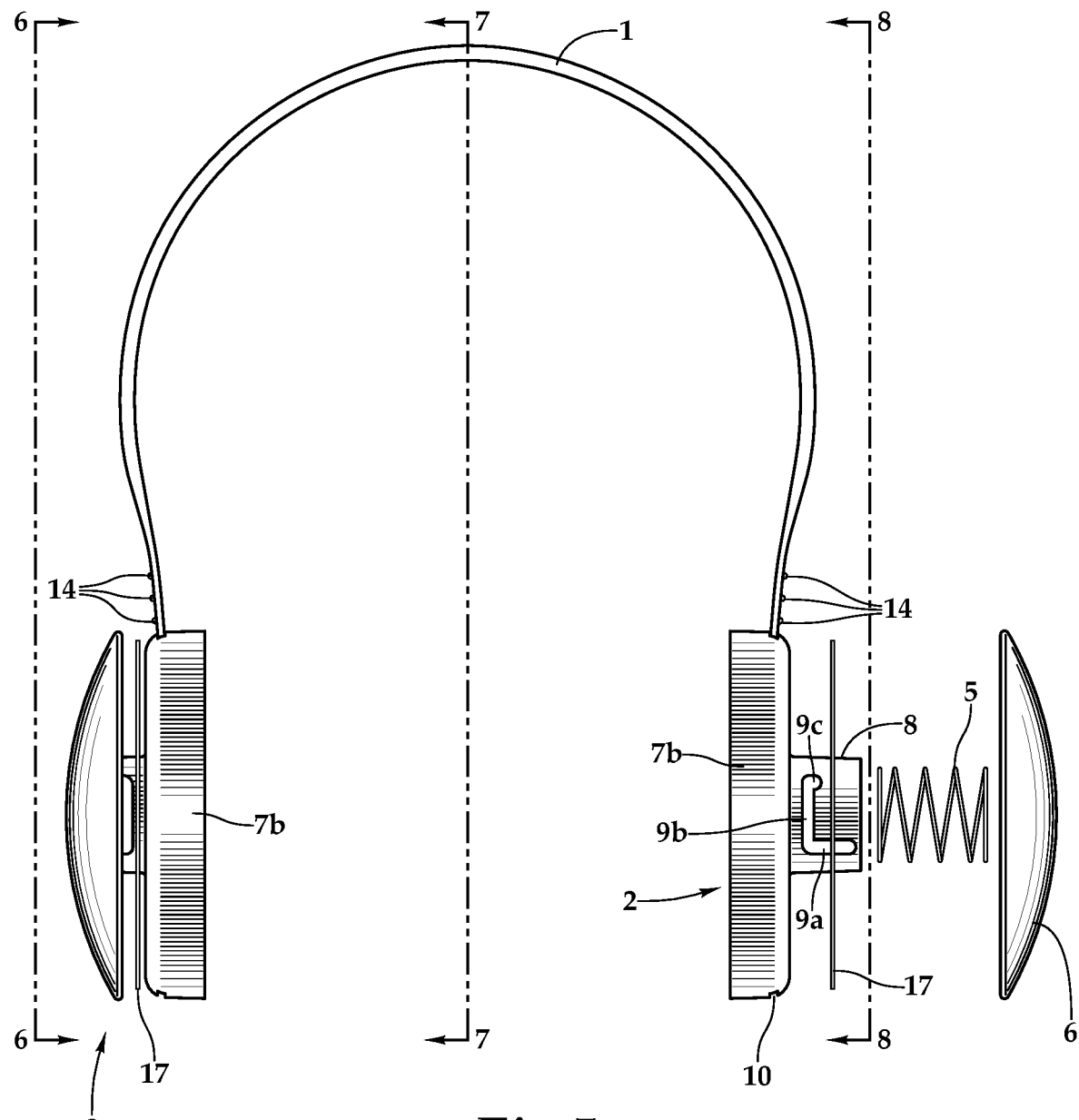
FIG. 5 is a front view of the present invention shown with one of the earmuff assemblies in an assembled and closed position and with the other earmuff assembly in a disassembled position. The inner and outer fabric coverings have been omitted from this figure for clarity.

FIG. 5 is a front view of the present invention shown with one of the earmuff assemblies in an assembled and closed position and with the other earmuff assembly in a disassembled position. As noted above, the inner and outer fabric coverings have been omitted from this figure for clarity, in this figure, the earmuff assembly 2 on the left-hand side of the figure is fully assembled and in a closed position. The earmuff assembly 2 on the right-hand side of the figure is in a disassembled position. As shown, in this figure and in FIG. 2, the spring 5 is configured to fit within the circular protrusion 8 on the inner earmuff assembly 4 and within the circular collar 15 on the outer earmuff assembly 6. In this manner, the spring 5 provides tension between the inner and outer earmuff assemblies.

FIG. 5 also provides a clear view of the L-shaped slot 9 in the circular protrusion 8 on the inner earmuff housing 4. Note that the L-shaped slot 9 has a first leg 9a that extends perpendicularly to the flat base plate 7a of the inner earmuff housing 4, a second leg 19 (connected at its end to the aforementioned first leg) that extends parallel to the flat base plate 7a of the inner earmuff housing 4, and a tab 9c that extends from the second end of the second leg in parallel with the first leg. Note that the tab 9c is not as long as the first leg 9a, however. This tab 9c acts as the locking mechanism for the outer earmuff housing 6, as explained more fully below.

FIG. 6 is a first side view of the present invention taken from the perspective shown in FIG. 5. As noted above, the inner and outer fabric coverings have been omitted from this figure for clarity. This figure shows the ridges 14 on the terminal end 2 of the arch-shaped member 1, as well as the convex surface of the outer earmuff housing 6.

FIG. 7 is a section view of the present invention taken from the perspective shown in FIG. 5. As noted above, the inner and outer fabric coverings have been omitted from this figure for clarity. This figure shows the linear alignment of the guide members 11, bracket 12 and slots 10 along the central axis of the inside surface of the inner earmuff housing 4.

FIG. 8 is a second side view of the present invention taken from the perspective shown in FIG. 5. As noted above, the inner and outer fabric coverings have been omitted from this figure for clarity. This figure shows the outside surface of the inner earmuff housing 4, including the circular protrusion 8, bracket 12 and slots 10.

FIG. 9 is an exploded side view of one of the earmuff assemblies of the present invention. This figure shows the inner fabric covering 19, the filler material 21, the inner earmuff housing 4, the optional cover plate 17, the spring 5, the outer earmuff housing 6, and the outer fabric covering 20.

FIG. 10 is a partially exploded side view of one of the earmuff assemblies of the present invention shown with the inner fabric covering and batting installed on the terminal earmuff housing. In this figure the inner fabric covering 19 has been wrapped around the filler material 21 and the inner earmuff housing 4 and adhered to the outside surface of the inner earmuff housing 4. The cover plate 17 is then affixed to the outside surface of the inner earmuff housing 4 to conceal the inner fabric covering 19.

FIG. 11 is a side view of one of the earmuff assemblies of the present invention shown in a fully assembled and closed position. In this figure, one end of the spring 5 has been placed inside of the circular protrusion 8, and the other end of the spring has been placed inside of the circular collar 15. The outer earmuff housing 6 is then press-fit onto the inner earmuff housing 4 with the keys 16 inserted into the first leg 9*a* of the L-shaped slot 9. At this point, the earmuff assembly is in an open position. In this position, the elasticized outer fabric covering 20 may be removed and replaced. Note that the spring 5 will maintain the earmuff assembly in an open position until manual pressure overcomes the force of the spring and the outer earmuff housing 6 is rotated on the inner earmuff housing 4. To close the earmuff assembly, manual pressure is applied to the outer earmuff housing 6, which is then rotated so that the key 16 travel inward along the first let 9*a*, and then transversely along the second leg 9*b* to the end of the second leg. When the manual pressure is released, the spring 5 then causes the key 16 to situate within the tab 9*c* of the L-shaped slot member, thereby locking the earmuff assembly in a closed position.

FIG. 12 is an exploded section view of one of the earmuff assemblies. As noted above, the inner and outer fabric coverings have been omitted from this figure for clarity. As shown in this figure, the circular collar 15 of the outer earmuff housing 6 is only as deep as the saucer-shaped outer earmuff housing 6; in other words, the height of the circular collar 15 is equal to distance "z" as indicated on FIG. 12.

FIG. 13 is a section view of one of the earmuff assemblies shown with the earmuff assembly in an open position. As noted above, the inner and outer fabric coverings have been omitted from this figure for clarity. In this figure, the two keys 16 are situated at the top of the first leg 9*a* of the L-shaped slot 9 in the circular protrusion 8 with the spring 5 maintaining the earmuff assembly in an open position.

FIG. 14 is a section view of one of the earmuff assemblies shown with the earmuff, assembly in a closed position. As noted above, the inner and outer fabric coverings have been omitted from this figure for clarity. In this figure, the keys 16 are positioned in the tabs 9*c* of the L-shaped slot members 9, as described above. FIGS. 12-14 were all taken from the perspective shown in FIG. 6.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A replaceable earmuff system comprising:
   (a) an arch-shaped member configured to fit over a wearer's head, the arch-shaped member comprising a first terminal end and a second terminal end;
   (b) a first earmuff assembly that is removably attached to the first terminal end of the arch-shaped member;
   (c) a second earmuff assembly that is removably attached to the second terminal end of the arch-shaped member; and
   (d) a spring;
   wherein each of the first and second earmuff assemblies comprises an inner earmuff housing, a spring, and an outer earmuff housing;
   wherein the inner earmuff housing is circular in shape and comprises a flat base plate and a lip that extends around a perimeter of a first side of the inner earmuff housing, the lip being perpendicular to the flat base plate;
   wherein a circular protrusion is situated in a center of the inner earmuff housing on a second side of the inner earmuff housing;
   wherein the circular protrusion comprises two opposing L-shaped slots;
   wherein the flat base plate comprises two opposing slots situated between the flat base plate and the lip;
   wherein the outer earmuff housing is saucer-shaped with a concave inner side and a convex outer side;
   wherein a circular collar is situated in a center of the concave inner side of the outer earmuff housing;
   wherein the circular collar has an inner diameter;
   wherein the circular protrusion on the inner earmuff housing has an outer diameter;
   wherein the inner diameter of the circular collar is greater than the outer diameter of the circular protrusion;
   wherein the circular collar comprises two opposing keys that are configured to fit within the L-shaped slots in the circular protrusion; and
   wherein the spring is configured to fit within the circular protrusion on the inner earmuff assembly and within the circular collar on the outer earmuff assembly when the system is fully assembled.

2. The replaceable earmuff system of claim 1, wherein the circular protrusion has a diameter, the flat base plate has a diameter, and the diameter of the circular protrusion is less than half of the diameter of the flat base plate.

3. The replaceable earmuff system of claim 1, wherein the flat base plate has an outer surface, and the walls of the circular protrusion are perpendicular to the outer surface of the flat base plate.

4. The replaceable earmuff system of claim 1, wherein the first side of the inner earmuff housing comprises two pairs of guide members that are configured to form a channel;
   wherein each pair of guide members comprises two guide members oriented parallel to one another;

wherein the two pairs of guide members are oriented so that one pair of guide members is linearly aligned with the other pair of guide members; and wherein the first and second terminal ends of the arch-shaped member each has a width;

wherein the width of the first terminal end is equal to the width of the second terminal end;

wherein there is a distance between each guide member in each pair of guide members; and wherein the distance between each guide member in each pair of guide member is equal to or greater than the width of the first or second terminal end of the arch-shaped member.

5. The replaceable earmuff system of claim 4, wherein a bracket is situated between the two pairs of guide members and configured to receive the first or second terminal end of the arch-shaped member;

wherein the first pair of guide members, the bracket, the second pair of guide members, and the opposing slots that are situated between the flat base plate and the lip of the flat base plate are all linearly aligned along a central axis of the inner earmuff housing.

6. The replaceable earmuff system of claim 1, wherein the inner earmuff housing has an outer diameter;

wherein the outer earmuff housing has an outer diameter; and wherein the outer diameter of the inner earmuff housing equals the outer diameter of the outer earmuff housing.

7. The replaceable earmuff system of claim 1, wherein the circular collar has a height;

wherein the circular protrusion has a height; and wherein the height of the circular collar is less than the height of the circular protrusion.

8. The replaceable earmuff system of claim 6, further comprising a cover plate;

wherein the cover plate has an outer diameter that is equal to the outer diameter of the inner earmuff housing and the outer diameter of the outer earmuff housing;

wherein the cover plate comprises a central bore with an inner diameter that is greater than the outer diameter of the circular protrusion; and wherein the cover plate is affixed to an outside surface of the inner earmuff housing between the inner earmuff housing and the outer earmuff housing.

9. The replaceable earmuff system of claim 1, further comprising an inner fabric covering that is configured to fit over the inner earmuff assembly and an outer fabric covering that is configured to fit over the outer earmuff assembly.

10. The replaceable earmuff assembly of claim 1, wherein each of the L-shaped slots in the circular protrusion comprises:

a first leg that extends perpendicularly to the flat base plate;

a second leg with a first end and a second end, the first end of the second leg being connected to the first leg, and the second leg extending parallel to the flat base plate; and a tab that extends from the second end of the second leg in parallel with the first leg.

\* \* \* \* \*